United States Patent [19]

Love et al.

[11] 4,061,651

[45] Dec. 6, 1977

[54] PREPARATION OF 3,5-DISUBSTITUTED-4-NITROISOXAZOLES

[75] Inventors: Richard F. Love, Fishkill; Roger G. Duranleau, Ardonia, both of N.Y.

[73] Assignee: Texaco Inc., New York, N.Y.

[21] Appl. No.: 685,221

[22] Filed: May 11, 1976

[51] Int. Cl.$^2$ .......................................... C07D 261/14
[52] U.S. Cl. ............................. 260/307 H; 260/592; 260/593 R
[58] Field of Search ..................................... 260/307 H

[56] References Cited

U.S. PATENT DOCUMENTS 3,466,296    9/1969    Plemmons ........................... 260/307

*Primary Examiner*—Raymond V. Rush
*Attorney, Agent, or Firm*—Thomas H. Whaley; Carl G. Ries; George J. Darsa

[57] ABSTRACT

3,5-disubstituted-4-nitroisoxazoles are prepared by catalytic condensation and dehydration of an alpha-nitroketone.

13 Claims, No Drawings

PREPARATION OF 3,5-DISUBSTITUTED-4-NITROISOXAZOLES

BACKGROUND OF THE INVENTION

This invention relates to a novel method of preparing 3,5-disubstituted-4-nitroisoxazoles from alpha-nitroketones. In particular, it relates to a method for preparing nitroisoxazoles by catalytic condensation and dehydration of alpha-nitroketones.

Nitroisoxazoles can be prepared by initially forming a 1,2-oxazole and thereafter nitrating the 4-position. One method by which 1,2-oxazoles can be prepared is by cyclization of monooximes of betadiketones with the simultaneous elimination of water. Nitration of the 4-position involves reaction of the 1,2-oxazole with nitric acid suitably in the presence of sulfuric acid at elevated temperatures. While such a two-step method provides some yield of the desired 4-nitroisoxazole, the starting materials are usually highly reactive and frequently form a mixture of products that are not readily separated. Further, the nitration step in many instances is non-selective in nitrating the 4-position, as for example when the oxazole contains acyl or phenyl substituents. When nitration of a phenylisoxazole is conducted, a mixture of aryl and isoxazole nitrosubstituted products are formed. Nitration of, for example, 3-acyl-5-alkylisoxazoles oxidizes the acyl group to a carboxylic acid group. Consequently the method is applicable to the preparation of a limited number of nitroisoxazoles. Each of the aforementioned disadvantages detract from the attractiveness of such processes.

It is therefore an object of this invention to provide a novel method for the preparation of disubstituted 4-nitroisoxazoles.

It is another object of this invention to provide a catalytic method for the preparation of disubstituted 4-nitroisoxazoles.

Yet another object of this invention is to provide a method for preparing disubstituted 4-nitroisoxazoles from alpha-nitroketones in a single step.

Other objects and advantages will become apparent from a reading of the following detailed description and examples.

SUMMARY OF THE INVENTION

Broadly, this invention contemplates a method for the preparation of 3,5-disubstituted-4-nitroisoxazoles which comprises catalytically condensing and dehydrating an alpha-nitroketone in a non-aqueous environment in the presence of a basic catalyst.

According to our invention, the alpha-nitroketones catalytically converted by condensation and dehydration in the instant invention correspond to the formula:

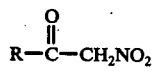

where R is an alkyl group having from 1 to 20 carbon atoms or an aryl group of from 6 to 20 carbon atoms. Illustrative of the alpha-nitroketones contemplated herein can be mentioned 1-nitro-2-propanone, 1-nitro-2-butanone, 1-nitro-2-pentanone, 1-nitro-2-hexanone, 1-nitro-2-heptanone, 1-nitro-2-octanone, 1-nitro-2-decanone, 1-nitro-2-dodecanone, 1-nitro-2-pentadecanone, 1-nitro-2-hexadecanone, 1-nitro-2-heptadecanone, 1-nitro-2-eicosanone, 1-nitro-2-heneicosanone, omega-nitroacetophenone, 4'-tertbutyl-2-nitroacetophenone, 2'-methyl-2-nitroacetophenone and omega-nitroacetonaphthone. Internal nitroketones, that is, nitroketones where the nitro group is on other than a terminal carbon, do not react in the instant method to produce the desired substituted nitroisoxazoles.

More specifically, the method of this invention comprises catalytically condensing and dehydrating the nitroketone or mixtures of nitroketones as hereinabove described at temperatures of from about 50° to 150° C., preferably from about 80° to 110° C. in the presence of a basic catalyst. The basic catalysts contemplated in the instant method are salts of weak acids and tertiary amines. The salts of weak acids employed as the catalyst include salts of the metals of Groups IA and IIA of the Periodic Table or of strongly basic ion exchange resins. The strongly basic ion exchange resins represent known materials that can be prepared by crosslinking of an olefinic monomer, such as ethylene, isobutylene, styrene or acrylic esters, with a cross-linking agent such as divinylbenzene or ethylene dimethacrylate to which has been added a monomer containing a quaternary ammonium group such as beta-trimethylammoniumethyl acrylate or beta-trimethylammoniumethyl methacrylate. The polymeric material is subsequently neutralized with a weak acid thereby forming the catalyst. Illustrative of the salt catalysts contemplated we mention sodium carbonate, sodium fluoride, sodium acetate, sodium decanoate, potassium carbonate, potassium fluoride, potassium acetate, potassium octanoate, lithium propionate, calcium fluoride, calcium propionate, strontium oxalate, barium fluoride and barium hexanoate. Other catalysts can be exemplified by such salts as the fluoride, carbonate or acetate of a strongly basic ion exchange resin.

As mentioned above, other basic catalysts encompassed by the present method are tertiary amines including aliphatic, aromatic and heterocyclic amines, tetraalkyl substituted alkylene diamines and tetraalkyl substituted guanidines exemplified by N-butyldidodecylamine, N,N-diethylcyclohexylamine, N,N-diethyldodecylamine, N,N-dimethylaniline, N,N-dimethylbenzylamine, N,N-dimethyloctylamine, N,N-diisopropylethylamine, N,N-dimethylethylamine, N,N-diethylmethylamine, N,N-ethylmethylpropylamine, N-ethyldibenzylamine, tributylamine, tridodecylamine, triethylamine, trihexylamine, trimethylamine, tricyclohexylamine, pyridine, methylpiperidine, 2-ethylpyridine, 1,4-dimethylpiperazine, 4-ethylpyridine, 2,4-ludidine, 3-picoline, 2,4,6-trimethylpyridine, quinoline, tetramethylethylenediamine, tetramethylpropylenediamine, tetramethylguanidine and tetraethylguanidine. In general, the tertiary amines employed as the basic catalyst in the instant method have from 3 to 36 carbon atoms.

As preferred catalysts in the method described herein we include carbonates, fluorides and salts of weakly acidic ion exchange resins of the metals sodium, potassium and calcium. The preferred catalysts are solids at room temperature and in many instances are poorly soluble in and easily recovered from the reactants and products described herein. Illustrative of the preferred catalysts are sodium carbonate, potassium carbonate, sodium fluoride, potassium fluoride, calcium fluoride and the sodium, potassium or calcium salts of weakly acidic ion exchange resins. The weakly acidic ion exchange resins represent known materials and can be prepared by a cross-linking of an unsaturated carboxylic acid, such as acrylic acid, methacrylic acid or maleic acid, with a cross-linking agent such as divinylbenzene or ethylene dimethacrylate or by condensation of resorcylic acid and formaldehyde. Highly preferred catalysts in the instant method are potassium fluoride and calcium fluoride.

The catalytic reaction is suitably conducted in the presence of a non-reactive polar organic solvent illustrated by 1,2-dimethoxyethane, diethylene glycol diethylether, dioxane, tetrahydrofuran, tertiary alcohols and mixtures thereof. A highly preferred solvent is tertiary butanol. Primary and secondary alcohols are deleterious in that they are reactive with the nitroketone and lead to the formation of esters. The reaction should also be conducted in an essentially non-aqueous environment, that is, in the substantial absence of water. The reaction described herein is sensitive to water and water introduced in amounts exceeding about 0.1 weight percent based on the weight of the nitroketone promote competing reactions and the formation of acids instead of the desired products. Moreover, water is a by-product of the condensation dehydration reaction and it is preferred to separate the water produced during the reaction as soon as practicable. For example, when a batch catalytic reaction is conducted, the water formed can be continuously removed from the reaction zone by conducting the method under partial refluxing conditions and at atmospheric pressure with continuous slow distillation of the reaction solvent. In continuous operations, as for example when the nitroketone is passed through a bed of basic catalyst, the water produced is separated from reaction product. Any unconverted nitroketone can be recycled for reintroduction through the catalyst bed.

The catalytic dehydration-condensation reaction described above provides 3,5-disubstituted-4-nitroisoxazoles corresponding to the formula:

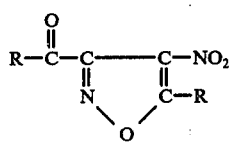

where R is as defined above. It will be understood that R can represent identical groups or different groups as when mixtures of nitroketones are employed. Illustrative of the nitroisoxazoles provided by the method include 3-acetyl-4-nitro-5-methylisoxazole, 3-propanoyl-4-nitro-5-ethylisoxazole, 3-butanoyl-4-nitro-5-propylisoxazole, 3-nonanoyl-4-nitro-5-octylisoxazole, 3-pentanoyl-4-nitro-5-butylisoxazole, 3-tridecanoyl-4-nitro-5-dodecylisoxazole, 3-benzoyl-4-nitro-5-phenylisoxazole, 3-[2-methylbenzoyl]-4-nitro-5-[2-methylphenyl]isoxazole, 3-[1-naphthanoyl]-4-nitro-5-[1-naphthyl]isoxazole and 3[4-tertiary butylbenzoy l]-4-nitro-5[4-tertiary butylphenyl] isoxazole. At the completion of the reaction the solvent if employed can be removed from the product by a low pressure distillation. Solid catalysts can be removed by filtration and those catalysts which are either liquids or soluble in the reaction product can be separated by evaportion at reduced pressures or by recrystallization of the isoxazole product using solvents in which the catalyst and the isoxazole product have greatly differing solubilities. Water soluble catalysts can be removed by water washing the evaporated residue.

The 4-nitroisoxazoles provided herein are useful as corrosion inhibitors and as additives to fuels and lubricants. The compounds are also useful as intermediates in the preparation of other valuable products as amine derivatives which are reported to have biological and physiological activity and other derivatives are useful as photographic sensitizers and dyes for color photography.

In order to more fully illustrate the nature of our invention and the manner of practicing the same, the following examples are presented.

EXAMPLE 1

A solution of 1-nitro-2-hexadecanone (14.25 grams, 50 mmoles) in tertiary butanol (75 milliliters, 0.95 moles) containing anhydrous potassium fluoride (0.2 grams, 3.44 mmoles) was refluxed for 3 hours. The tertiary butanol was removed from the reaction at 30°–35° C. under a reduced pressure of 30 millimeters. A dark semi-solid residue (15.5 gram) after fractional crystallization from methanol and subsequently from petroleum ether afforded 5.93 grams of product having a melting point of 67°–68° C. Infrared spectrum, nuclear magnetic resonance and mass spectrometry analyses identified the product as 3-pentadecanoyl-4-nitro-5-tetradecylisoxazole.

EXAMPLE 2

A solution of 1-nitro-2-tetradecanone (13.0 grams, 50 mmoles) in tertiary butanol (75 milliliters, 0.95 mole) containing anhydrous potassium fluoride (0.2 gram, 3.44 mmoles) was refluxed for 3 hours with the slow removal of 25 milliliters of tertiary butanol. The residual solvent was stripped from the reaction mixture by evaporation at 30°–35° C. under a reduced pressure of 30 millimeters. The evaporation residue was recrystallized from petroleum ether to afford 4.4 grams of 3-tridecanoyl-4-nitro-5-dodecylisoxazole having a melting point of 60°–62° C.

EXAMPLE 3

A blend of 1-nitro-2-decanone (10.1 grams, 50 mmoles), tertiary butanol (100 milliliters, 1.26 moles) and anhydrous potassium fluoride (0.2 gram, 3.44 mmoles) was refluxed for 6 hours at 83°–85° C. The butanol was then removed by evaporation under reduced pressure (25° C. at 20 mm.) and the semi-solid residue, after repeated crystallization from methanol, afforded 1.2 grams of 3-nonanoyl-4-nitro-5-octylisoxazole having a melting point of 40°–41° C. An uncrystallized fraction consisted of a mixture of isoxazole and nonanoic acid.

EXAMPLE 4

A blend of 1-nitro-2-decanone (10.1 grams, 0.05 mole), 100 milliliters of isopropylalcohol and 0.2 gram of anhydrous potassium fluoride were refluxed for 2 hours. The isopropylalcohol was substantially removed by distillation at atmospheric pressure and the remainder removed by evaporation at 30 mm. pressure leaving 9.8 grams of residue. The residue was mixed in benzene and the recovered residue after evaporation of the solvent weighed 9.5 grams. The residue was determined by infrared and nuclear magnetic resonance spectroscopy to consist of 16 weight percent isopropylnonanoate, 46 weight percent nonanoic acid and 36 weight percent 3-nonanoyl-4-nitro-5-octylisoxazole.

We claim:

1. A method for the preparation of 3,5-disubstituted-4-nitroisoxazoles which comprises contacting an alpha-nitroketone corresponding to the formula:

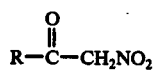

where R is an alkyl group having from 1 to 20 carbon atoms or an aryl group from 6 to 20 carbon atoms in a non-aqueous environment at a temperature of from about 50° to 150° C. with a basic catalyst, wherein said catalyst is a carbonate, fluoride, oxalate or $C_{2-10}$ alkanoate of a metal of Group IA or IIA of the Periodic Table or a carbonate, fluoride, oxalate or $C_{2-10}$ alkanoate of a strongly basic ion exchange resin, or a tertiary amine.

2. A method according to claim 1 wherein the catalytic reaction is conducted at a temperature of from about 80° to 110° C.

3. A method according to claim 1 wherein said nitroketone is 1-nitro-2-hexadecanone.

4. A method according to claim 1 wherein said nitroketone is 1-nitro-2-tetradecanone.

5. A method according to claim 1 wherein said nitroketone is 1-nitro-2-decanone.

6. A method according to claim 1 wherein said nitroketone is omega-nitroacetophenone.

7. A method according to claim 1 wherein said nitroketone is omega-nitroaceto-(4-tertiarybutyl)phenone.

8. A method according to claim 1 wherein said catalyst is potassium fluoride.

9. A method according to claim 1 wherein said catalyst is calcium fluoride.

10. A method according to claim 1 wherein the catalytic reaction is conducted in the presence of a non-reactive polar solvent.

11. A method according to claim 10 wherein said solvent is tertiary butanol.

12. A method according to claim 1 wherein by-product water is continuously separated from the reaction product.

13. A method for the preparation of 3,5-disubstituted-4-nitroisoxazoles which comprises contacting an alpha-nitroketone corresponding to the formula:

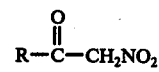

where R is an alkyl group having from 1 to 20 carbon atoms in a non-aqueous environment at a temperature of from about 50° to 150° C. with a basic catalyst, wherein said catalyst is a tertiary amine.

* * * * *